US008685067B2

(12) United States Patent
King et al.

(10) Patent No.: US 8,685,067 B2
(45) Date of Patent: Apr. 1, 2014

(54) COMPRESSION PLATE APPARATUS

(75) Inventors: Bruce King, Tucson, AZ (US); Omar Contento, Hillsboro, OR (US); Mike Lanham, Tucson, AZ (US); Lloyd Champagne, Phoenix, AZ (US)

(73) Assignee: Competitive Global Medical, LLC, Tucson, AZ (US)

(*) Notice: Subject to any disclaimer, the term of this patent is extended or adjusted under 35 U.S.C. 154(b) by 145 days.

(21) Appl. No.: 13/326,068

(22) Filed: Dec. 14, 2011

(65) Prior Publication Data
US 2012/0197303 A1 Aug. 2, 2012

Related U.S. Application Data

(60) Provisional application No. 61/425,468, filed on Dec. 21, 2010.

(51) Int. Cl.
*A61B 17/58* (2006.01)
*A61B 17/80* (2006.01)

(52) U.S. Cl.
USPC .......................................... 606/282; 606/291

(58) Field of Classification Search
USPC ............. 81/57, 57.12–57.14, 57.22, 57.26, 81/57.28–57.32; 606/70–71, 280, 286, 606/281–282, 289, 291
See application file for complete search history.

(56) References Cited

U.S. PATENT DOCUMENTS

| | | |
|---|---|---|
| 2,390,461 A | 12/1945 | Racz |
| 4,119,092 A * | 10/1978 | Gil .................................. 606/96 |
| 4,304,011 A | 12/1981 | Whelan, III ...................... 3/1.91 |
| 4,352,212 A | 10/1982 | Greene et al. ..................... 3/1.91 |
| 4,759,768 A | 7/1988 | Hermann et al. ............... 623/21 |
| 4,946,455 A | 8/1990 | Rosen ........................... 604/403 |
| 5,011,497 A | 4/1991 | Persson et al. ................... 623/21 |
| 5,074,882 A | 12/1991 | Grammont et al. |
| 5,129,903 A | 7/1992 | Luhr et al. ........................ 606/71 |
| 5,147,386 A | 9/1992 | Carignan et al. ............... 623/21 |
| 5,251,520 A | 10/1993 | Lanham |

(Continued)

FOREIGN PATENT DOCUMENTS

| | | | |
|---|---|---|---|
| EP | 904740 A2 * | 3/1999 | |
| EP | 1 632 200 | 3/2006 | ............... A61F 2/42 |

(Continued)

OTHER PUBLICATIONS

International Search Report and Written Opinion issued in PCT Application Serial No. PCT/US10/46870 on Oct. 20, 2010, 12 pgs.

(Continued)

*Primary Examiner* — Nicholas Woodall
*Assistant Examiner* — Larry E Waggle, Jr.
(74) *Attorney, Agent, or Firm* — Hayes Soloway P.C.

(57) ABSTRACT

The present invention provides a system, including methods, apparatus and kits for stabilizing and compressing bone fractures using a compression plate apparatus for stabilizing bone fragments with compression comprising a plate having at least two bone screw holes adapted to accept at least one bone screw each, the plate additionally having at least one elongate hole through the plate; a rack comprising rack teeth located along at least one linear edge of the elongate hole; a pinion axle assembly comprising a pinion axle having a head portion, a pinion gear having complementary gear teeth for engaging the rack teeth and a lower portion having threads for engaging bone.

23 Claims, 18 Drawing Sheets

(56) References Cited

U.S. PATENT DOCUMENTS

| | | | |
|---|---|---|---|
| 5,334,184 A | 8/1994 | Bimman | |
| 5,417,692 A | 5/1995 | Goble et al. | 606/73 |
| 5,522,903 A | 6/1996 | Sokolow et al. | 623/21 |
| 5,569,247 A | 10/1996 | Morrison | 606/61 |
| 5,591,166 A | 1/1997 | Bernhardt et al. | 606/61 |
| 5,628,740 A | 5/1997 | Mullane | 606/61 |
| 5,667,510 A | 9/1997 | Combs | |
| 5,683,466 A | 11/1997 | Vitale | 623/18 |
| 5,713,897 A | 2/1998 | Goble et al. | 606/53 |
| 5,827,285 A | 10/1998 | Bramlet | 606/60 |
| 5,984,970 A | 11/1999 | Bramlet | 623/21 |
| 6,284,001 B1 | 9/2001 | Knapp | 623/21.14 |
| 6,689,169 B2 | 2/2004 | Harris | 623/21.16 |
| 6,733,502 B2 | 5/2004 | Altarac et al. | 606/61 |
| 6,767,351 B2 | 7/2004 | Orbay et al. | 606/69 |
| 6,780,186 B2 | 8/2004 | Errico et al. | 606/71 |
| 7,608,096 B2 | 10/2009 | Foley et al. | 606/280 |
| 7,717,958 B2 | 5/2010 | Cragg et al. | 623/17.12 |
| 7,740,648 B2 | 6/2010 | Young et al. | 606/286 |
| 2002/0198527 A1 | 12/2002 | Muckter | 606/73 |
| 2005/0055023 A1 | 3/2005 | Sohngen et al. | |
| 2005/0216008 A1 | 9/2005 | Zwirnmann et al. | 606/69 |
| 2006/0235414 A1 | 10/2006 | Lim et al. | 606/73 |
| 2006/0271054 A1 | 11/2006 | Sucec et al. | 606/73 |
| 2007/0027230 A1 | 2/2007 | Beyar et al. | 523/117 |
| 2007/0055236 A1 | 3/2007 | Hudgins et al. | 606/61 |
| 2007/0185584 A1 | 8/2007 | Kaufmann et al. | 623/21.15 |
| 2007/0270855 A1 | 11/2007 | Partin | |
| 2007/0282342 A1 | 12/2007 | Niederberger et al. | 606/73 |
| 2008/0065224 A1 | 3/2008 | Reigstad et al. | 623/18.11 |
| 2008/0140130 A1 | 6/2008 | Chan et al. | 606/280 |
| 2008/0195156 A1 | 8/2008 | Ainsworth et al. | 606/279 |
| 2008/0234678 A1 | 9/2008 | Gutierrez et al. | 606/60 |
| 2008/0300634 A1 | 12/2008 | Gray | 606/280 |
| 2009/0062868 A1 | 3/2009 | Casutt | 606/316 |
| 2009/0112269 A1 | 4/2009 | Lieberman et al. | 606/301 |
| 2009/0210016 A1 | 8/2009 | Champagne | 606/309 |
| 2009/0234359 A1* | 9/2009 | Onoue et al. | 606/71 |
| 2009/0264934 A1 | 10/2009 | Youssef et al. | 606/280 |
| 2010/0004691 A1 | 1/2010 | Amato et al. | 606/280 |
| 2011/0004255 A1 | 1/2011 | Weiner et al. | 606/301 |

FOREIGN PATENT DOCUMENTS

| | | | | |
|---|---|---|---|---|
| FR | 2 651 119 | 8/1989 | | A61F 2/42 |
| FR | 2 692 776 | 6/1992 | | A61F 2/42 |
| WO | WO 95/33425 | 12/1995 | | A61F 2/42 |
| WO | WO 97/22301 | 6/1997 | | A61B 17/00 |
| WO | WO 02/30262 | 4/2002 | | |
| WO | WO 05/41793 | 5/2005 | | A61F 2/44 |
| WO | WO2010047688 | 4/2010 | | A61B 17/58 |
| WO | WO 2010/026371 | 11/2010 | | |

OTHER PUBLICATIONS

International Search Report and Written Opinion of the International Searching Authority issued in related PCT application PCT/US2011/028646 dated May 3, 2011 (12 pgs).

Office Action, U.S. Appl. No. 13/049,363, dated Oct. 16, 2012 (34 pgs).

* cited by examiner ental Patent Application Ser. No. 61/425,468, filed Dec. 21, 2010, which is incorporated by reference herein.

COMPRESSION PLATE APPARATUS

CROSS REFERENCE TO RELATED APPLICATIONS

This application claims priority to U.S. Provisional Patent Application Ser. No. 61/425,468, filed Dec. 21, 2010, which is incorporated by reference herein.

BACKGROUND

1. Field of the Invention

The present invention is in the field of Orthopedic implants, and in particular is directed to a novel yet simple bone plate improvement whereby a controllable compression capability is instilled in the bone plate.

2. Description of the Related Art

Bone plates are well-known in the Orthopedic arts, having been used to repair skeletal system injuries or corrective modifications since the earliest days of orthopedic surgery. Bone plates are also the subject of numerous patents, with over 130 issued US patents issued with the term "bone plate" in their titles since 1976. Generally, a bone plate is a stiff yet malleable low-profile shaped element with perforations for accepting bone screws or anchors. Usually metallic in nature, a boneplate is used to stabilize one or more bones that have been fractured in accidents and that need temporary or permanent external support during the healing process. Bone plates have been created for just about any bone fracture situation imaginable, from typical long bone fractures that occur in the femur to specialized plates devised to stabilize various vertebrae of the spinal column.

A typical modern bone plate is depicted in U.S. Pat. No. 7,740,648 (Young et al.) that is directed to a bone plate apparatus particularly suited to tibial plateau-leveling osteotomy and a distal femoral osteotomy. The bone plate has a main longitudinal axis, a bone-contacting bottom side (not shown) and a top side with at least three sets of overlapping holes which communicate through the plate from the top to the bottom side. The sets of overlapping holes define threaded apertures having multifaceted surfaces. When applied to a bone, two sets of such overlapping holes are located so as to lie on opposite sides of an osteotomy site and on the tibial plate; a third is aligned at approximately 60 degrees with the longitudinal axis. Compression of bone fragments is described at the fracture site across the line 112 when bone screws 24 having beveled surfaces 120 and 122 (preferably having no thread 30 on the head 26) enter the apertures and are torqued down such that wedging action takes place at the interface between the beveled surfaces and the chamfered surfaces 102 and 104. The degree of wedging attainable by this design is limited by careful prepositioning and installation because there is little ability to change the degree of wedging after installation except by advancing or reversing the screws which could impact the final plate-bone conformity.

What is needed is a simple yet reliable device for applying lateral stability and adjustable compression to a fracture or osteotomy site that does not rely upon bone anchor placement.

BRIEF SUMMARY OF THE INVENTION

The problem of not being able to attach a bone plate and apply variable compression to the fragments attached to the plate is addressed by adding a rack-and-pinion device to the plate thereby allowing the surgeon to precisely meter the amount of compressive pressure to the fracture or osteotomy site.

An embodiment of the invention is directed to a compression plate apparatus for stabilizing bone fragments with compression comprising a plate having at least two bone screw holes adapted to accept at least one bone screw each, the plate additionally having at least one elongate hole through the plate; a rack comprising rack teeth located along at least one linear edge of the elongate hole; a pinion axle assembly comprising a pinion axle having a head portion, a pinion gear having complementary gear teeth for engaging the rack teeth and a lower portion having threads for engaging bone, whereby when a first bone screw is anchored in bone through a bone screw hole in the plate and the pinion axle assembly is anchored in a portion of bone across a fracture from the anchored bone screw through the elongate hole in the plate, then rotation of the pinion gear causes sliding motion of the unanchored bone fragment relative to the plate.

Another embodiment of the invention is directed to a composite compression plate apparatus for stabilizing at least one bone fracture with compression comprising a plurality of compression plate apparatus of claim 1. The composite apparatus is configured by assembling or manufacturing two or more of the individual compression plates as one so that compression may be achieved in more than one direction, or to compress across more than one fracture point. For example, a compression plate shaped in the form of a "Y," "T" or an "H", each arm having a compression feature in it, would allow flexible use of such a composite device.

DETAILED DESCRIPTION OF EMBODIMENTS OF THE INVENTION

Figure 1:
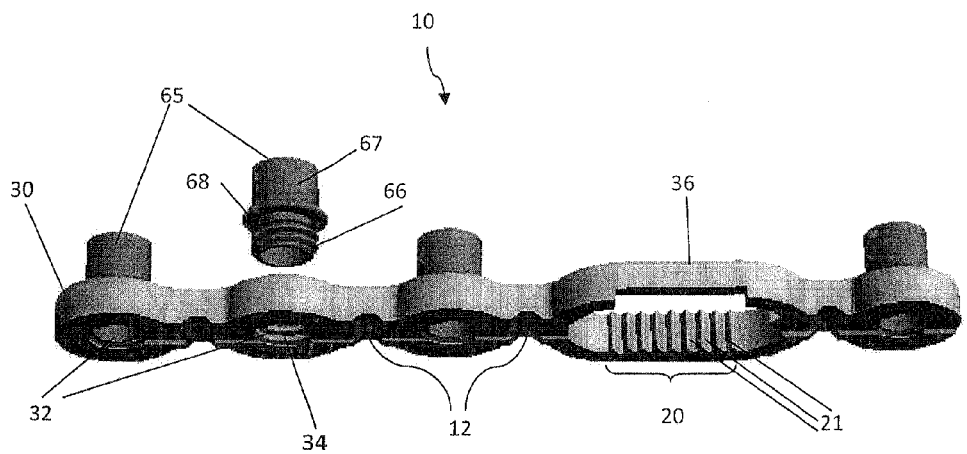
FIGS. 1 and 2 are elevational perspective computer-assisted drawings ("CADs") of an embodiment of the compression plate shown with three of four drill guide inserts installed and 1 hovering above the plate.

The various embodiments of the present invention provide a system, including methods, apparatus and kits for connecting bones and/or bone portions or fragments using a compression plate apparatus that enables the application of specific amounts of compression to a fractured bone or bones that does not rely upon angular placement of the bone screws or anchors. The problem in the art being addressed by the embodiments of the present invention is that of aligning and compressing a bone with one or more fractures or multiple fragments of a single bone that could benefit from a degree of compression of the bones at the fracture site. It is well-known to orthopedic surgeons that applying a small amount of compression to bones aids in enhanced knitting of the bone thereby increasing the chances of an optimal patient recovery and reducing time spent in hospital (Wolff's Law). Attempts to "angle" the bone screws anchoring a bone plate to a fracture site are often used to generate a degree of compression between the bone fragments. This is an inexact method that relies largely upon the skill and experience of the surgeon to utilize the available bone plate hole geometry, and so an optimal outcome is not guaranteed.

The present invention solves this problem by providing a compression plate apparatus for stabilizing bone fragments with compression comprising a plate having at least two bone screw holes adapted to accept at least one bone screw each, the plate additionally having at least one elongate hole through the plate; a rack comprising rack teeth located along at least one linear edge of the elongate hole; a pinion axle assembly comprising a pinion axle having a head portion, a pinion gear having complementary gear teeth for engaging the rack teeth and a lower portion having threads for engaging bone, whereby when a first bone screw is anchored in bone through a bone screw hole in the plate and the pinion axle assembly is anchored in a portion of bone across a fracture from the anchored bone screw through the elongate hole in the plate, then rotation of the pinion gear causes sliding motion of the unanchored bone fragment relative to the plate.

A "fracture" is a well-known term in the Orthopedics art and generally refers to a crack, or complete break in a bone resulting in separation of the cracked bone into two or more portions or fragments. A fracture is illustrated in the figures beginning at FIG. 13 as numeral 17. The compression plate of the present invention is used to aid in stabilizing a fracture or bone fragments by first setting the bones in the correct position, then positioning the plate over the area containing the fracture and placing screws through the plate to secure it to the bones thereby holding them together for at least the duration of the healing process. The plate, being made of a rigid material, adds strength to the broken bone to enable healing of the bone without deformity. In order for a prior art bone plate to function to position and stabilize a fracture there must be at least two holes, one on a first side of the fracture, the second on the opposite side of the fracture. Generally there are at least two holes on either side of the fracture, but a functional minimum is one. The hole through which the first screw is driven into the bone secures the plate to one of the bone fragments, and the second screw then serves to lock into position the plate across the fracture. However, there is no means to compress the bone fragments except for angling the bone screws, thereby adding a small, uneven compression effect. In one embodiment of the present invention the elongate hole serves as the source of compression by adding a rack-and-pinion feature as shown throughout most of the Figures. In one embodiment the elongate hole has gear-type teeth either attached or machined into a linear portion of the hole, thereby defining the rack portion. A pinion axle assembly comprising a pinion head, an intermediate portion comprising a pinion axle having a freely rotating pinion gear (FIGS. 5-6, 9) and a threaded end is then driven into the unattached bone through the elongate hole and when the pinion gear is rotated, the bones are brought into compression. At this time another bone screw is driven through a bone screw hole in the plate on the unanchored side of the plate thereby immobilizing the plate relative to the fracture site while the two bone fragments are still in compression. It is apparent from this general description of the function of the compression plate that the elongate hole can be located anywhere on the plate so long as room is left for bone screw holes on both sides of the fracture.

Now with respect to FIGS. 1-4, compression plate assembly 10 is conventionally a metallic structure having a length, width and thickness. The dimensions are selected to fit the specific application. One of ordinary skill in the art of bone plate design will have the knowledge to select the appropriate dimensions to effect the goals of stabilizing a fracture or osteotomy site based on the size and thickness of the bone involved, the number of fractures, and the strength required. Conventional materials include stainless steel, titanium and alloys thereof, with other materials being possible as described at length below. The plate has a top surface and a bottom surface, with each having distinct functions. In the present embodiment the top surface faces away from the bone and normally does not contact it. The bottom surface is normally in contact with bone and so may have distinct features for that purpose. For example, there are two channels cut into the bottom of plate 30 for purposes of facilitating manual bending for custom fitting of the plate to the patient. Longitudinal channel 14 is imposed along the length (or longitude) of the plate while latitudinal channel 12 appears at points between the bone plate holes 32 and cuts across the plate bottom surface in a cross-wise or latitudinal aspect. The sides of these channels are shown as substantially orthogonal to the bottom surface of the plate, but the sides may form an angle other than ninety degrees. Equivalent features that may also selectively weaken the plate for bending include holes or perforations either entirely or only partially through the plate, selectively thinned areas, or v-shaped troughs.

The compression plate assembly 10 has holes 32 along its length and through the plate 30 to accommodate bone screws 90 or anchors that are used to attach the plate to the surface of the bone under repair. "Holes" as they are used here means a substantially circular opening in the plate that perforates the entire thickness of the plate. The holes 32 are configured to accept bone screws 90 or anchors. The holes may be configured to accept bone screws that do not lock into the plate, or they may be adapted to lock the screw head directly to the plate. In the locking screw case the plate and screw have features such as complementary bone screw hole threads 34 that facilitate the locking function. In the current embodiment, the bone screw hole threads 34 shown in FIGS. 1-4 are complementary to the threads 66 of the bone screw drill guide 65. The drill guide 65 threads into the hole substantially as shown and provides the necessary support for a drill bit when pre-drilling bone to accept a bone screw. In the case where the bone screw does not lock into the plate, then the screw threads on the shaft of the screw engage the bone only and the screw head having a flange larger in diameter than the diameter of the hole will compress the plate against the bone as the screw is driven further into the bone to its limit as the plate is compressed against the bone.

The compression plate apparatus may also have an elongated hole 36 that resembles a slot with round corners or an oval racetrack. One embodiment of the elongate hole has substantially semi-circular edges and a portion between the circular edges that has straight or parallel walls. However, the semi-circular edges are not mandated, and may be replaced by straight edges in other embodiments. In one embodiment the elongate hole penetrates the entire thickness of the plate from top to underside. In other embodiments the hole may have a partial shelf feature, open in the middle, and extending across the bottom of the hole like a racetrack around the edge of the hole. The elongate hole of the present embodiment has a set of features that together comprise the rack portion of the device. In FIGS. 1-4 are shown a set of rack teeth 21 which may be conventional gear teeth adapted to engage other similar gear teeth. The rack teeth 21 provide a surface upon which the teeth of a pinion gear may engage and convert the rotational motion of the engaged pinion gear to linear motion of the object connected to the rack, in this case the compression plate. The exact type or conformation of the rack teeth is not important so long as the pinion gear teeth chosen to engage the rack teeth complement the rack teeth. The rack teeth may be machined from the surface of the elongate hole or they may comprise a separate part to be affixed to the inner surface of the rack. Given that there will be minimal wear of the rack teeth, a preferred embodiment is to simply machine the teeth from the rack surface.

Figure 2:
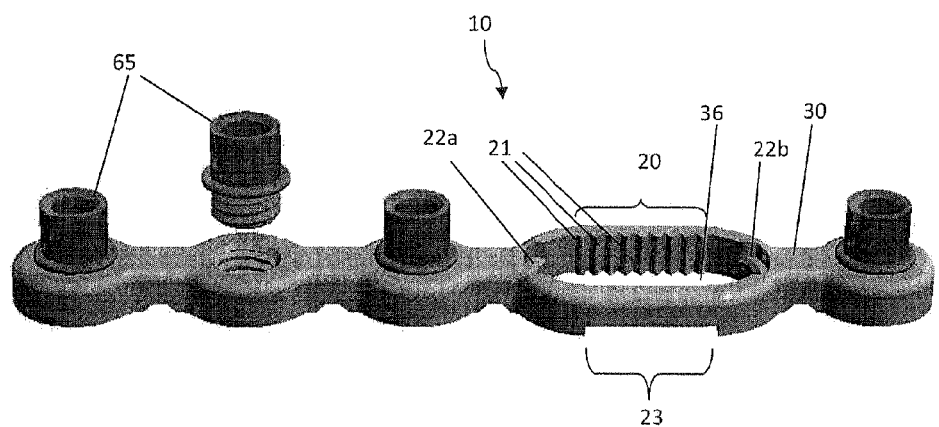
Figure 3:
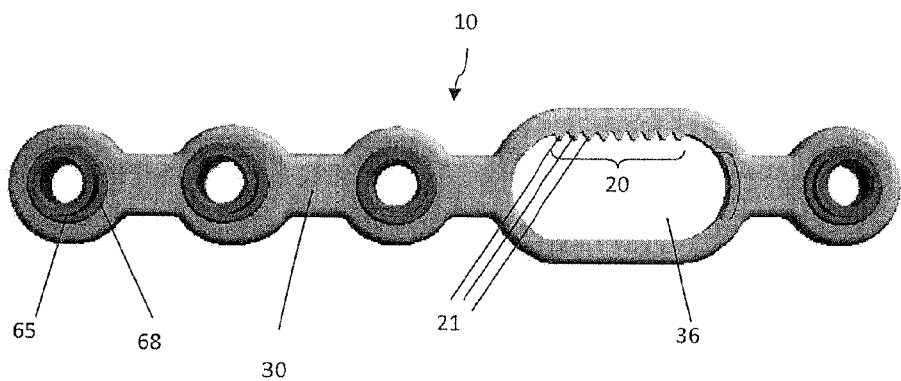
FIGS. 3 and 4 are top-down and bottom-up, respectively, CADs of an embodiment of the compression plate.
Figure 4:
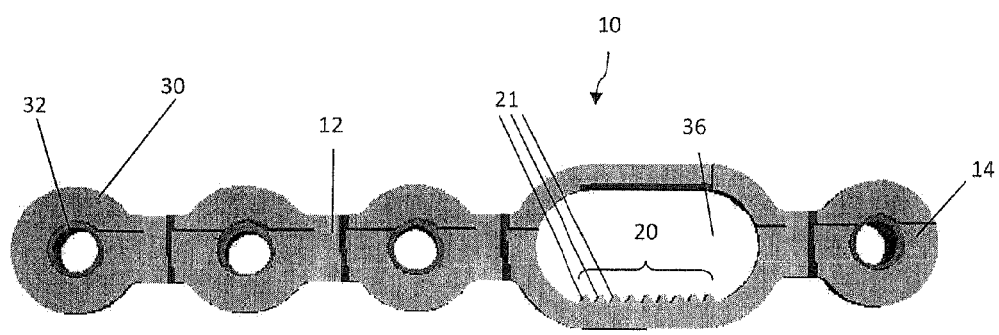
Figure 16:
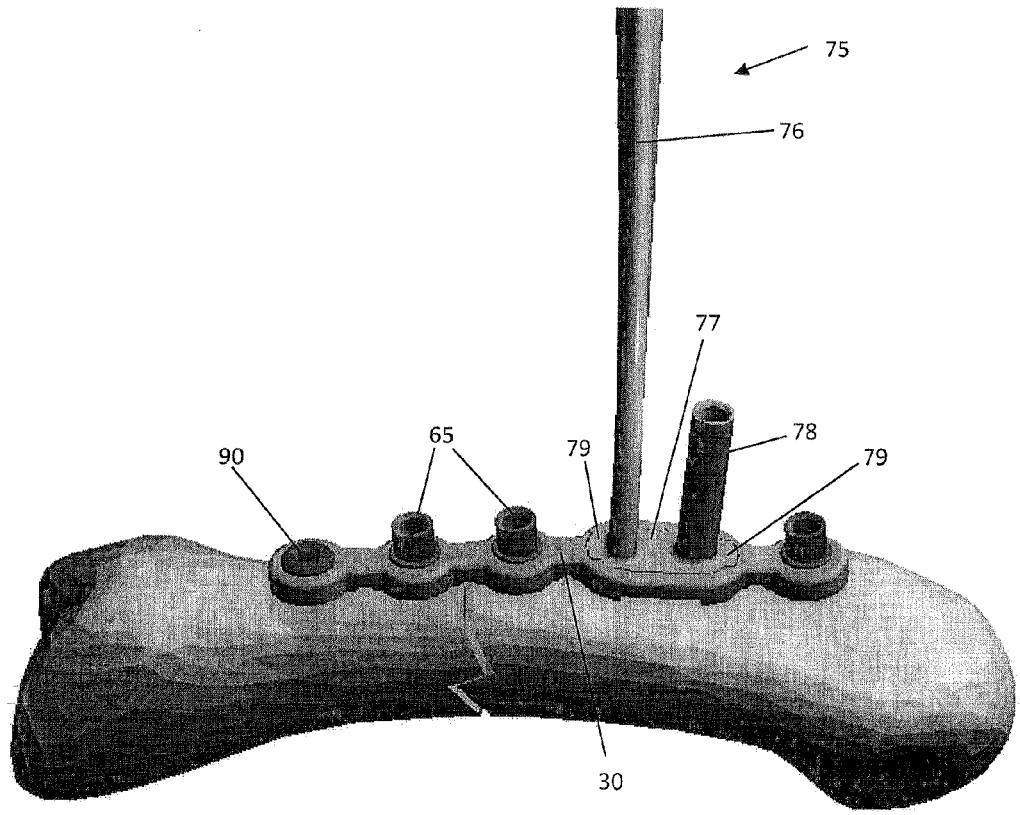
FIG. 16 is the same elevational perspective as FIG. 15 except that a drill guide assembly has been installed in position D.

In one embodiment there are three cutouts from the surfaces of the compression plate 30 that abut elongate hole 36. Insert positioning cutouts 22a,b (FIG. 2) are on the top side of the plate and abut the elongate hole on its longitudinal edges opposite each other. They are designed to accommodate the tabs of the various drill guides and inserts that seat within the elongate hole, thereby aiding in correct positioning of the drill guide tools and/or inserts. The third cutout is drill guide cutout 23 which is a cutout from the bottom surface and abuts the elongate hole 36 as also shown in FIG. 2. Drill guide cutout 23 accommodates the forward tab 74 on the rack insert drill guide 70 and the forward tab 79 on pinion placement drill guide 75 (FIG. 16).

Figure 5:
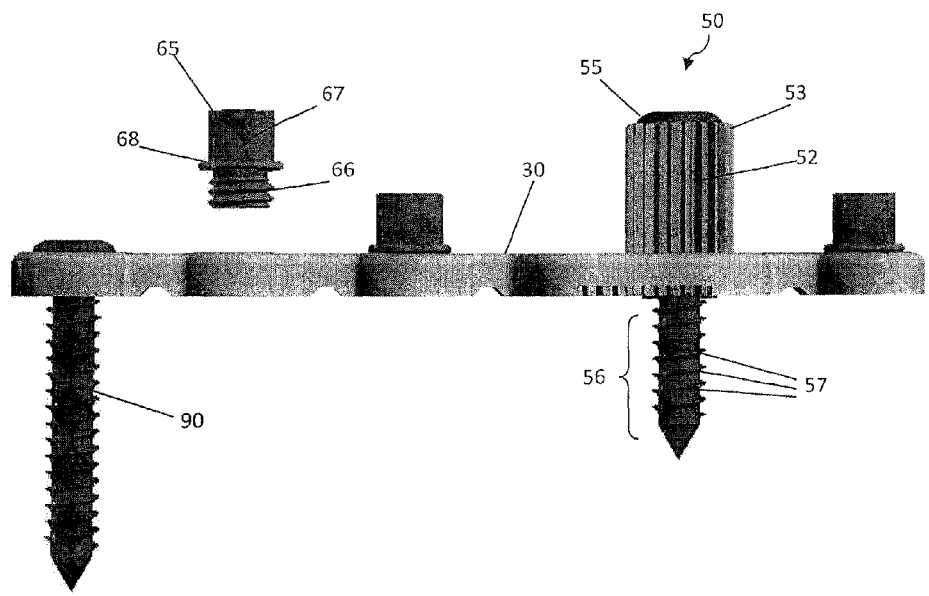
FIGS. 5 and 6 are edge-on and elevated CADs, respectively, of an embodiment of compression plate, with a first bone screw in the installed position and the pinion axle assembly shown engaging the elongate hole/rack.
Figure 6:
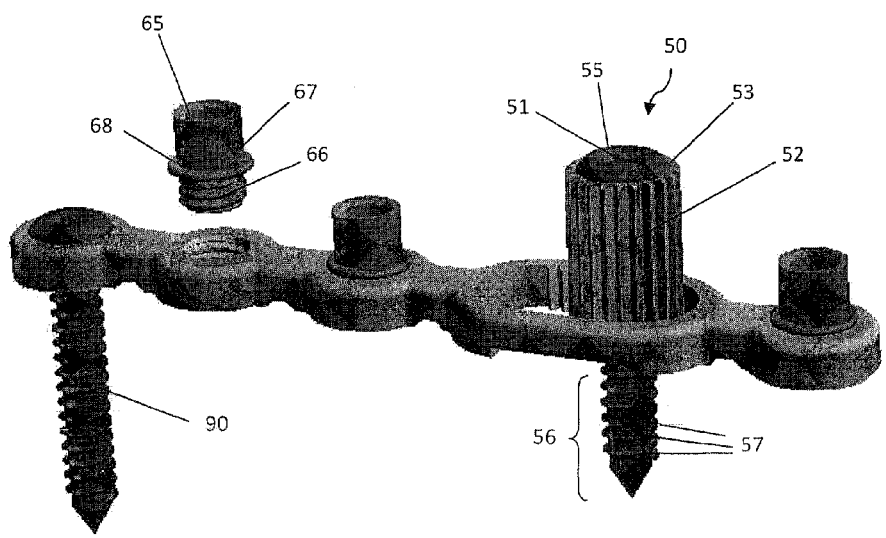
Figure 27:
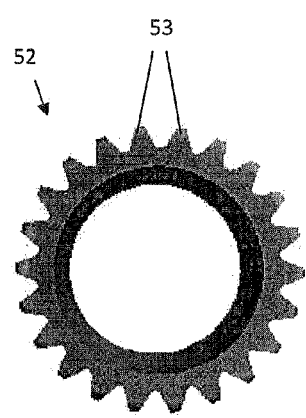
FIGS. 27 and 28 are end-on and side perspectives of a CAD rendering of the pinion gear 52.
Figure 28:
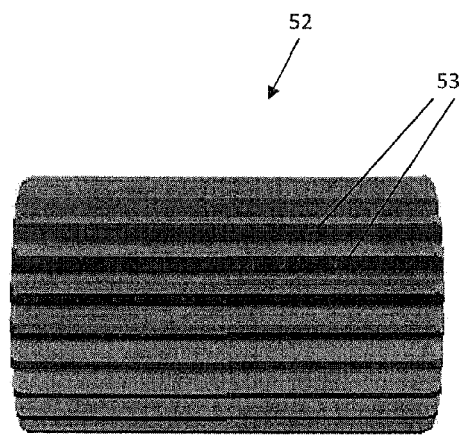
Figure 29:
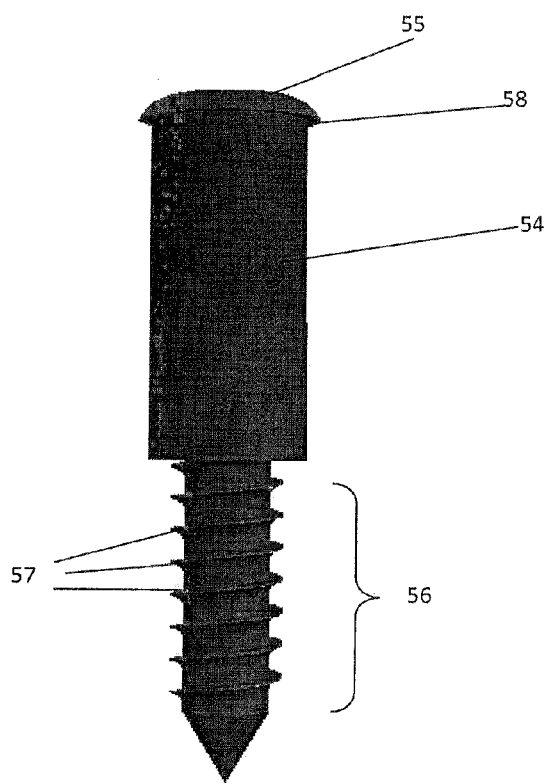
FIG. 29 is a CAD rendering of the pinion axle assembly without the gear in place.

FIGS. 5 and 6 are edge-on and elevational perspective CADs, respectively of an embodiment of the compression plate assembly 10, with a first bone screw 90 in the installed position and the pinion axle assembly 50 is shown engaging the elongate hole/rack combination. Pinion axle assembly 50 is shown in more detail in FIGS. 27-29. The pinion axle assembly comprises two parts, the pinion axle 54 (FIG. 29) and the pinion gear 52. In FIGS. 27-28 pinion gear 52 is shown from two different perspectives: FIG. 27 shows the pinion gear looking down through its central axis, and FIG. 28 shows the gear from the side. The pinion gear teeth 53 are visible from both perspectives. Gear teeth 53 mesh with rack teeth 21 and so have complementary characteristics. Pinion gear 52 has an internal diameter that is slightly larger than the external diameter of the intermediate portion of pinion axle 54 which is where the gear rides when installed. In operation as shown in FIGS. 5-6, the pinion gear 52 rotates axially about pinion axle 54. The pinion gear may travel up and down somewhat on pinion axle 54, and will normally bottom out on the upper bone surface and top out at the pinion head lip 58, whose outer circumference is greater than the internal diameter of the gear, thereby acting as a travel limiter. In an alternative embodiment, the partial shelf feature will serve to limit pinion gear downward travel as the gear teeth will ride on the shelf at the gear's lower limit. The up-and-down travel of the gear on the pinion axle is incidental to its operation. Pinion head 55 also has a drive pattern 51 for accepting any standard driver such as a square drive for applying torque to the pinion during installation and removal. Finally, pinion axle assembly 50 has a pinion threaded end 56 having pinion threads 57 adapted to engage bone.

Figure 7:
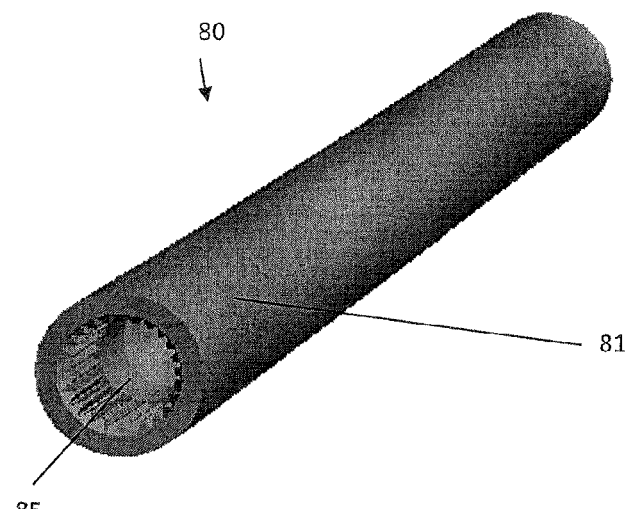
FIGS. 7 and 8 are longitudinal and end-on CADs, respectively, of the pinion driver tool.
Figure 8:
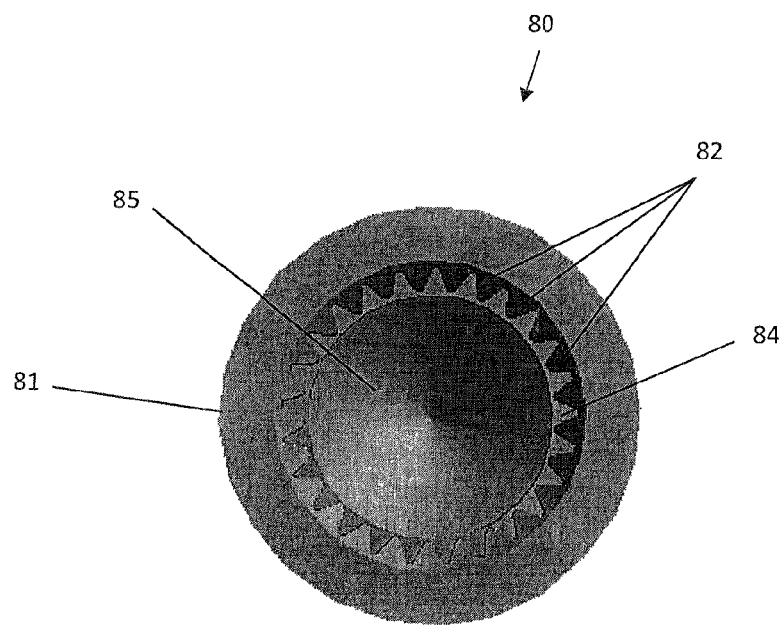
Figure 9:
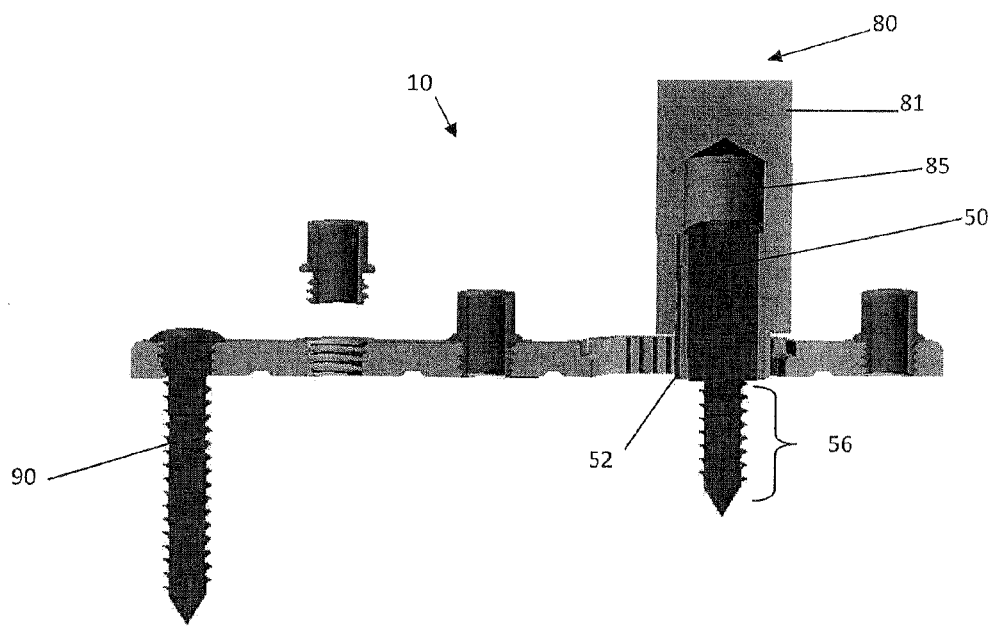
FIG. 9 is a cross-section of the compression plate of FIG. 5 or 6.
Figure 10:
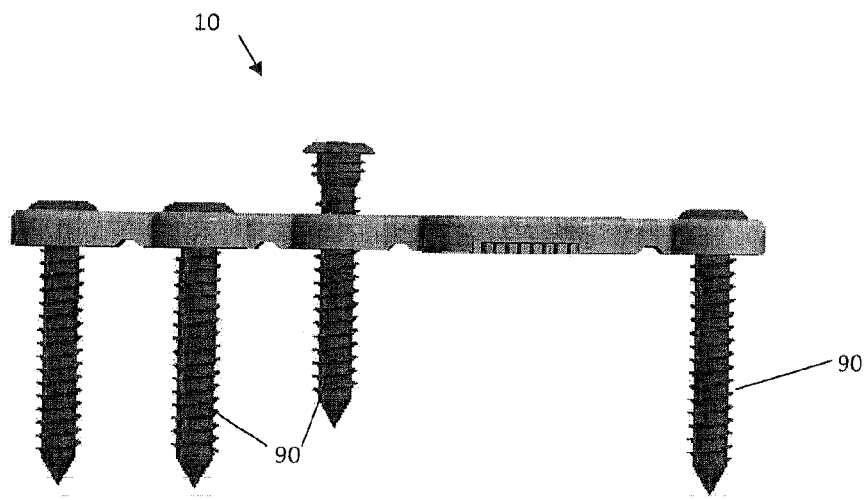
FIG. 10 is a depiction of a partially installed compression plate with positions A, B and E filled, and position C (See FIG. 12 for position labels) in the process of being filled. Note that the bone screws have threaded heads and lock into the compression plate.
Figure 11:
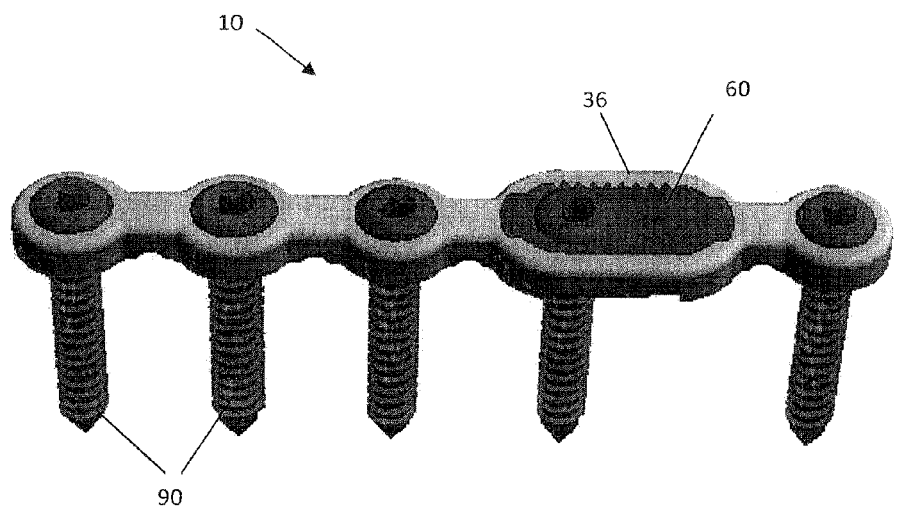
FIG. 11 is an elevational perspective of a CAD rendering of an installed compression plate having five screws using a 1-screw rack insert 60.

FIGS. 7 and 8 are longitudinal and end-on CADs, respectively, of the pinion drive tool. The pinion drive tool has an internal drive pattern complementary to the pinion gear teeth 53 so that the drive tool may mesh with them when placed over the pinion gear and pushed down over the pinion axle assembly, as shown in cross-section in FIG. 9. FIG. 9 shows the pinion driver tool 80 fully engaged with pinion axle assembly 50 and ready to be rotated. Pinion drive tool 80 comprises a pinion driver tool body 81, pinion driver tool teeth 82, a handle 83 (FIGS. 19-20), an internal shoulder 84 which serves to limit the depth the tool can descend on the pinion axle assembly, and a lumen 85. In operation, pinion driver tool 80 is rotated which thereby rotates in turn the pinion gear 52, which moves the rack in a linear fashion. This action is shown more fully in the installation procedure.

Another embodiment of the present invention is a locking feature that allows the installing surgeon to apply compression through rack-and-pinion gear rotation, then lock and/or unlock the degree of compression thereby allowing removal of his hands from the device yet maintaining compression. The locking/unlocking functions can be accomplished through numerous embodiments. For example, in one embodiment the pinion gear locks/unlocks either directly to the rack or to the non-rack part of the plate. In another embodiment the pinion gear may lock to the pinion axle about which it rotates. In yet another embodiment the driver tool locks and unlocks the pinion gear from the rack. In still another embodiment the driver tool locks/unlocks the pinion gear from pinion axle. In the latter instance, the driver tool can free-wheel the pinion gear when placed over the gear, and when the driver tool is removed the pinion gear locks to the pinion axle again. The locking components would be contained within the pinion axle assembly.

In another embodiment the driver tool can lock/unlock the pinion gear to the rack, or to the pinion axle, and the locking components are contained within the driver tool. In some embodiments the pinion gear can turn in the direction of compression, but cannot turn back. In yet other embodiments the pinion gear can ratchet in either direction. In yet another embodiment flexure of the rack can lock the pinion gear to the rack or the pinion axle. In another embodiment the pinion gear can lock in any position, not dependant on detent.

One embodiment is a locking pawl. The pawl may be located on the rack where it can engage with the teeth of the pinion gear. The pawl removes the necessity of having an assistant maintain torque on the pinion driver to maintain compression while the surgeon installs the remaining bone screws, thus reducing the likelihood of the compression being varied from the optimal amount when the surgeon must remove his hands from the driver to prepare to install the remaining bone screws. Pawls are well-known in the art and it is well within the skill in the art to design numerous pawls for this function.

Another embodiment for locking the compression is to provide a mechanism for locking the pinion gear to the pinion axle. A freewheeling clutch or similar mechanism would allow free rotation of the pinion gear in one direction, and reversing the direction would automatically lock the pinion gear to the pinion axle. A Sprag-type clutch is one particular design that would effectuate this result. Sprag clutches are available from GMN Bearing USA Ltd., Houston, Tex. A release for the sprag clutch could also be provided in the situation where overcompression had occurred and the surgeon desired to release all compression and start the compression phase over.

Another embodiment of the present invention is a combination of two or more compression plates arranged in shapes conducive to repair of complex or multiple fractures. Such a composite compression plate apparatus comprises a plurality of compression plates arranged in patterns such as an "H," "T," "Y" or even circular patterns resembling a snowflake. Each projecting arm may have its own elongate hole and bone screw holes, thereby enabling compression in multiple dimensions. Examples of such composite plates are shown in FIGS. 34-37. Any number of multi-armed plate designs can be envisioned, limited only by the desired repair application.

The compression plate may be formed of any suitable biocompatible material. Exemplary biocompatible materials include (1) metals (for example, titanium or titanium alloys; alloys with cobalt and chromium (cobalt-chrome); stainless steel; etc.); (2) plastics (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or zirconia, among others); (4) composites; and/or the like. In some examples, these materials may form the body of the compression plate and/or a coating thereon. The choice of materials is generally within the skill of a person having ordinary skill in the art of implantable medical devices.

Each compression plate apparatus may be formed by any suitable process(es). Exemplary processes include EDM, molding, machining, casting, forming, crimping, milling, and/or the like. Threads, teeth or other retention structures on the compression plate may be formed at the same time as and/or after formation of other portions of the plate. One having ordinary skill in the machining arts will have the requisite skill to select the most appropriate methods for creating the compression plate given the guidance provided herein.

The compression plate apparatus of the current invention may be used in any situation in which stabilization and compression of two adjacent bones is desired. For example, if a fracture without complete separation ("greenstick fracture") occurs, normally there is no need for an open reduction procedure, but in the event the fracture is reduced via surgery then it may be desired to use a bone plate to assist healing by applying compression to the two fragments. In a compound or other type of complete break fracture, one or more bone plates are sometimes necessary to provide the required stability and alignment for the extended period of healing required.

Figure 12:
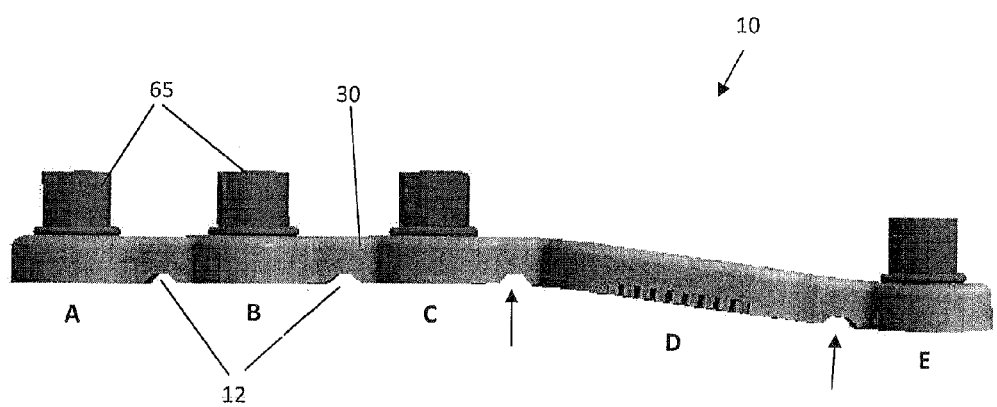
FIG. 12 is an edge-on perspective of a CAD rendering of a bent compression plate.

Installation of the compression plate involves the following steps. Reference is made throughout the installation procedure to an embodiment of the invention that has four bone screw holes and one elongate hole with rack, as described in the Figures. FIG. 12 shows the embodiment having 5 positions, with the positions and their correlating screw types and installation order shown in Table 1 below.

TABLE 1

| Positions within Rack Plate | Placement Order | Type of screw |
|---|---|---|
| A | 1 | Bone Screw |
| B | 4 | Bone Screw |
| C | 5 | Bone Screw |
| D | 2 | Pinion Axle Assembly |
| D | 6 | Rack Insert with 2 Bone Screws |
| E | 3 | Bone Screw |

Other embodiments can have from a minimum of 2 holes for accepting bone screws and one elongated hole/rack to unlimited combinations of racks and bone screw holes in any number of shapes. See, for example, FIGS. 34-37.

Figure 13:
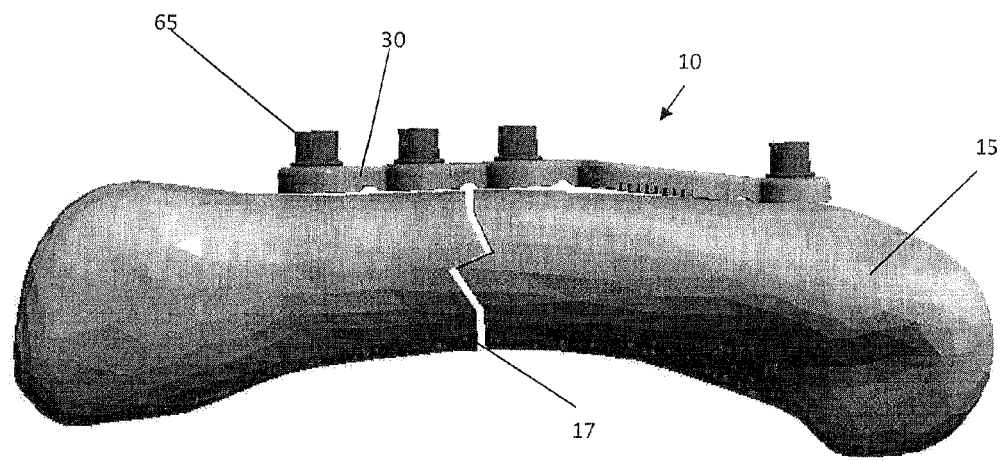
FIGS. 13 and 14 are edge-on and top-down views of the compression plate of FIG. 12 superimposed on a fractured bone 15.
Figure 14:
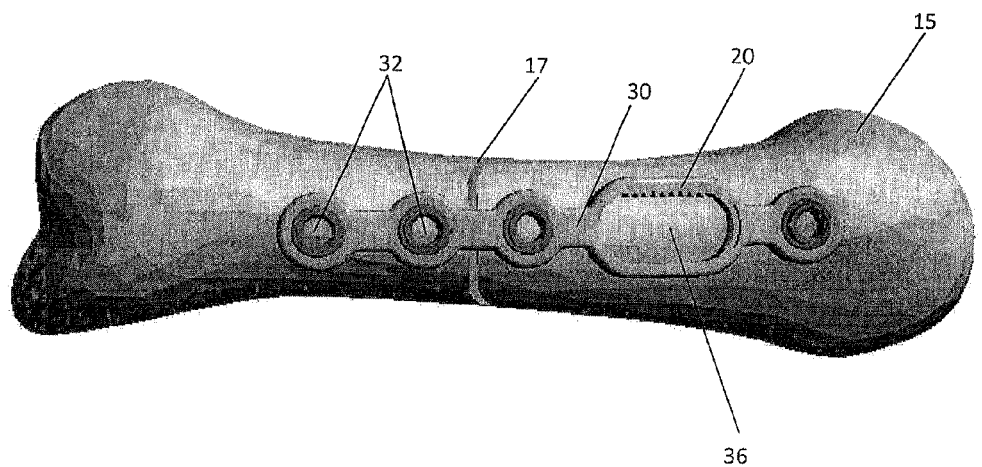
Figure 15:
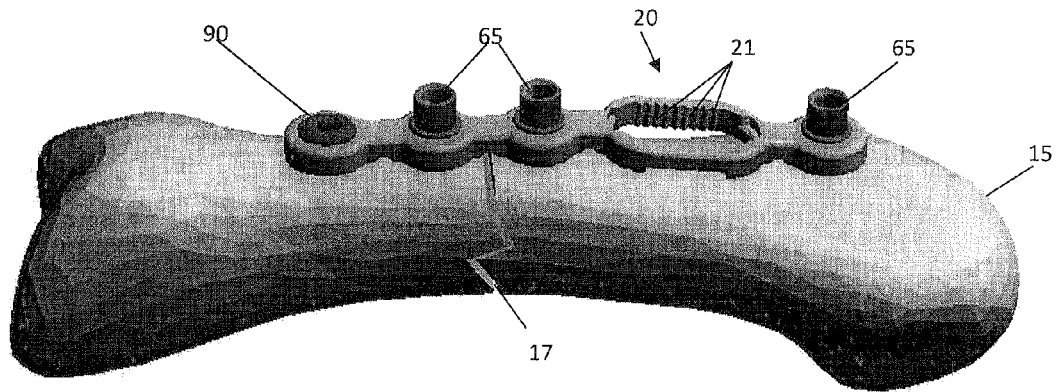
FIG. 15 is a elevational perspective of the compression plate of FIG. 14 with a bone screw installed in position A.

Unless otherwise indicated the sequence of steps is an important criteria for a successful installation. The first step, which is not a part of the invention is to surgically prepare the site. In exposing the bone in preparation for the plate, selection of the proper plate size will be important to speed the procedure once underway. Next, pre-bend the compression plate to the likely contour found at the fracture site. FIG. 12 shows a compression plate that has been bent at the two latitudinal channels indicated by the arrows. Next, set the bone. This may involve pulling apart or retracting the bones slightly if they are not perfectly aligned. After they have been aligned they are ready for a plate. Place the compression plate in location against the bone with the fracture centered between positions B and C. FIG. 13 shows a compression plate of the present embodiment of the invention placed on a computer-aided depiction of a bone 15. Next, adjust the plate in situ to match the bone contour. It is recommended but optional that all holes mentioned hereafter have a pilot hole pre-drilled with drill guides 65 to ensure proper positioning. Next drive the first screw 90 into position A of the compression plate 30. The installed screw 90 is shown in FIG. 15. Tighten the screw 90 to pull the plate 30 to the bone 15 so that it is immobilized for the next step. FIG. 16 shows an installed pinion placement drill guide assembly 75 that facilitates pre-drilling the pinion location pilot hole accurately within the bone 15. Pre-drill the pilot hole through pinion placement drill guide 78.

Figure 17:
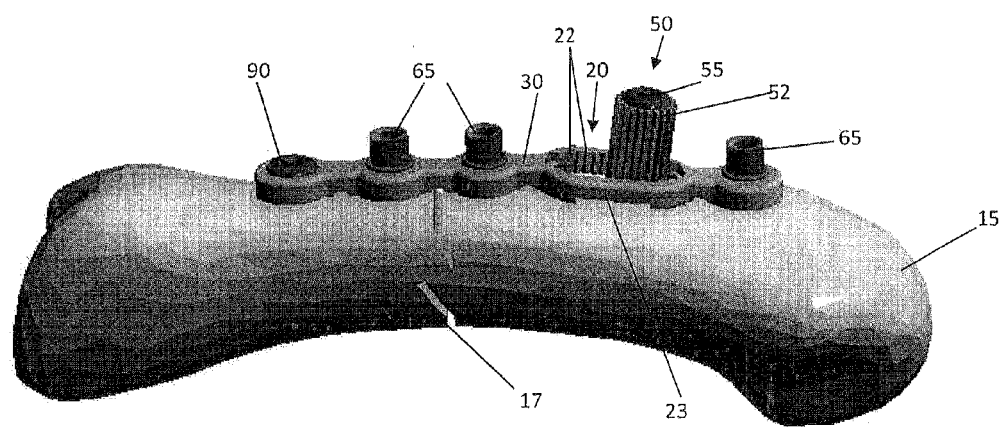
FIGS. 17 and 18 are elevational and top-down perspectives of a CAD rendering of the compression plate of FIG. 16 except that a pinion axle assembly has been installed in position D.
Figure 18:
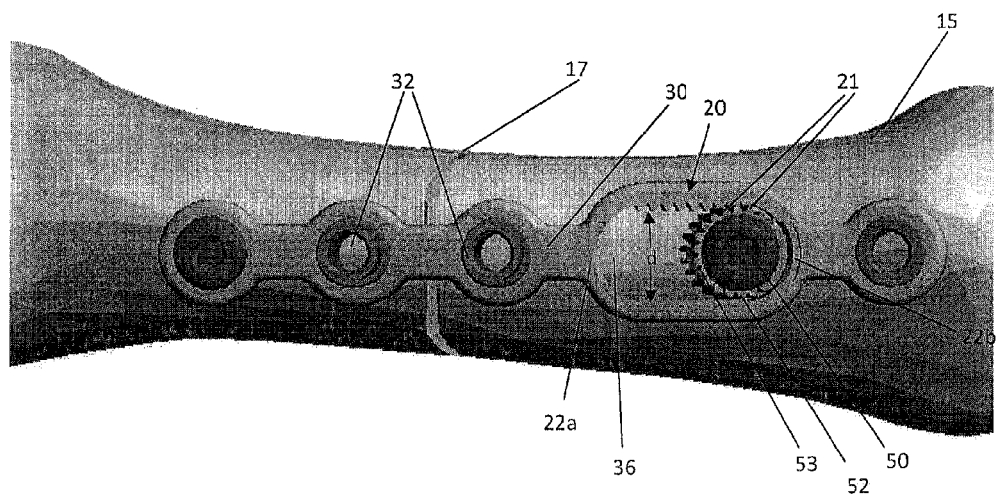

Next, drive the pinion axle assembly 50 into the pilot hole as shown in FIGS. 17-18. The pinion drive pattern in pinion head 55 as shown is a square drive so a square drive tool is indicated, however the design of the compression plate and accompanying pinion axle assembly is not so limited. As indicated from the top-down view of FIG. 18 pinion axle assembly 50 has a pinion gear 52 with pinion gear teeth 53 that engage the rack teeth 21. It is to be noted that the linear portion of the opposite walls of the elongate hole where the rack is located need to be maintained a preset distance apart so that the gear teeth and rack teeth are maintained in engaging position. That distance ("d" in FIG. 18) may vary slightly, but must be slightly larger than the outside diameter of the pinion gear, but not so large as to allow the teeth to become disengaged. The tolerance for this distance varies based on the size of the application. For example, a thick, broad plate for stabilizing a femur will necessarily require a stronger rack-and-pinion than that required for a smaller plate and smaller bones. Also, the angle of the teeth, their depth and related criteria will also change based on the amount of torque that the application will require. One of ordinary skill in the mechanical arts familiar with rack-and-pinion design criteria will be able to design a distance d into the specific application which will allow rotation.

Figure 19:
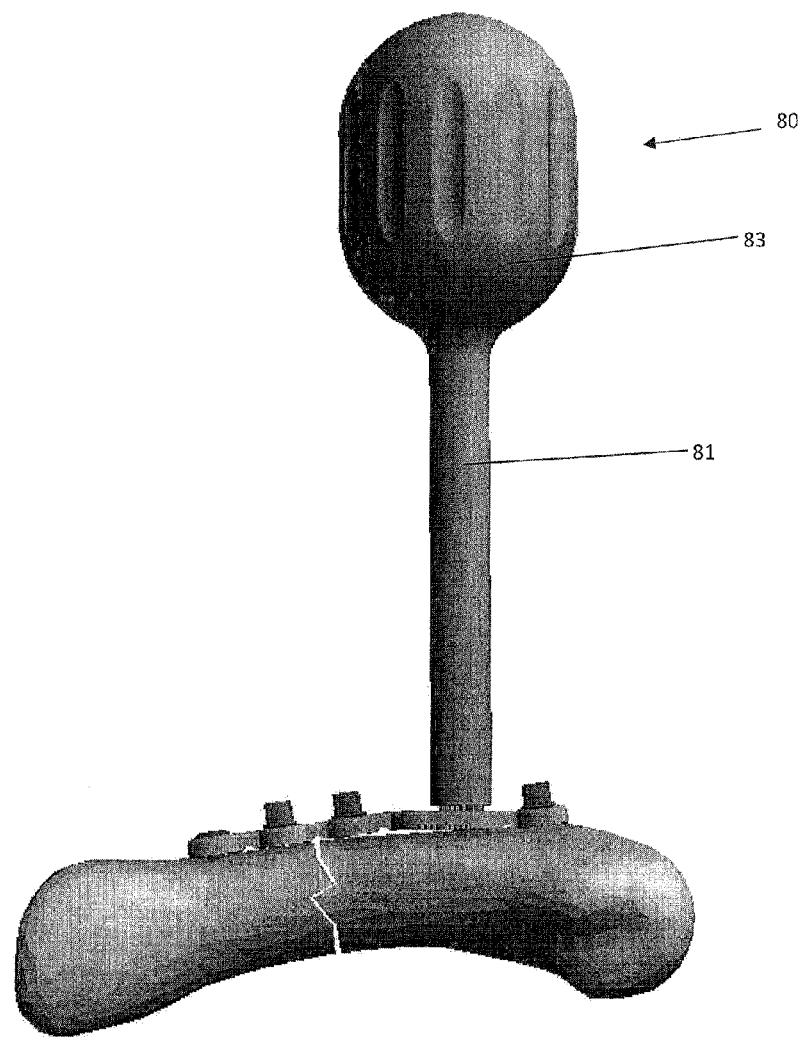
FIGS. 19 and 20 are edge-on and elevational perspectives of CAD renderings of the compression plate of FIG. 17 with a driver tool 80 installed over the pinion axle assembly.
Figure 20:
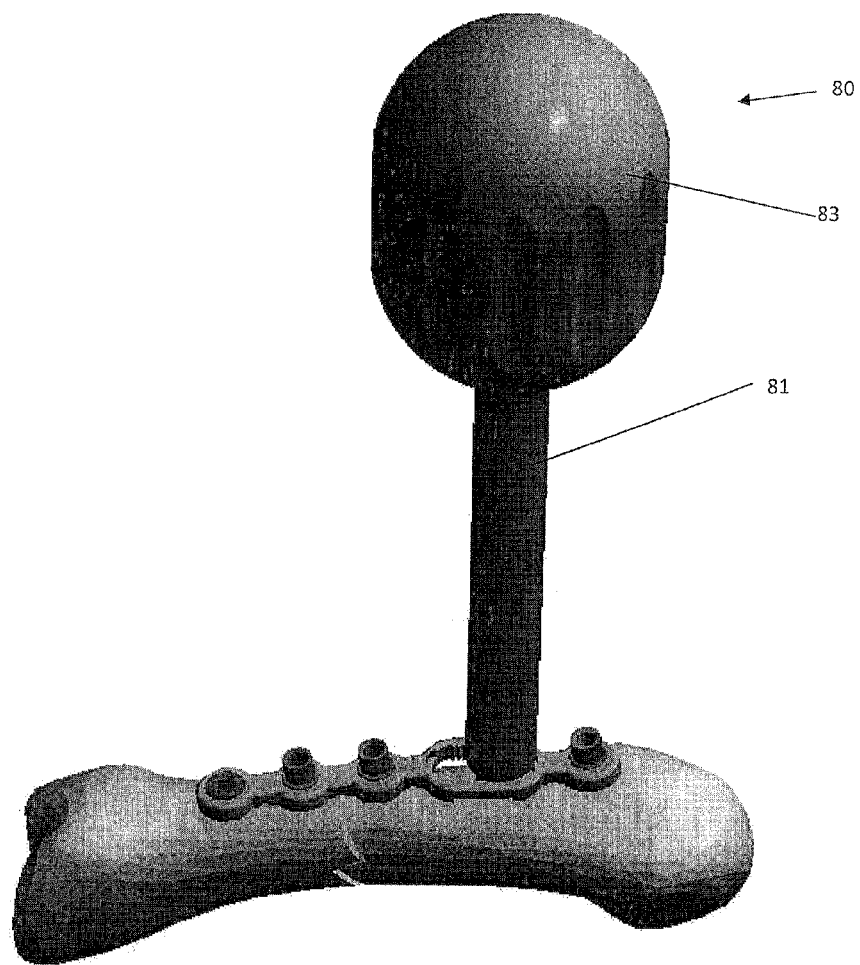
Figure 21:
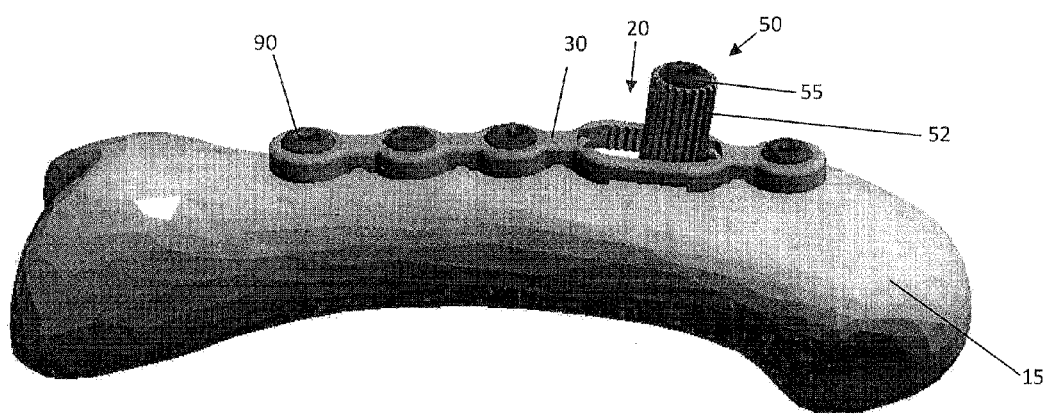
FIG. 21 is an elevational perspective of the compression plate with bone screws installed in positions A, B, C and E and the pinion axle assembly is still in position D.
Figures 22, 23:
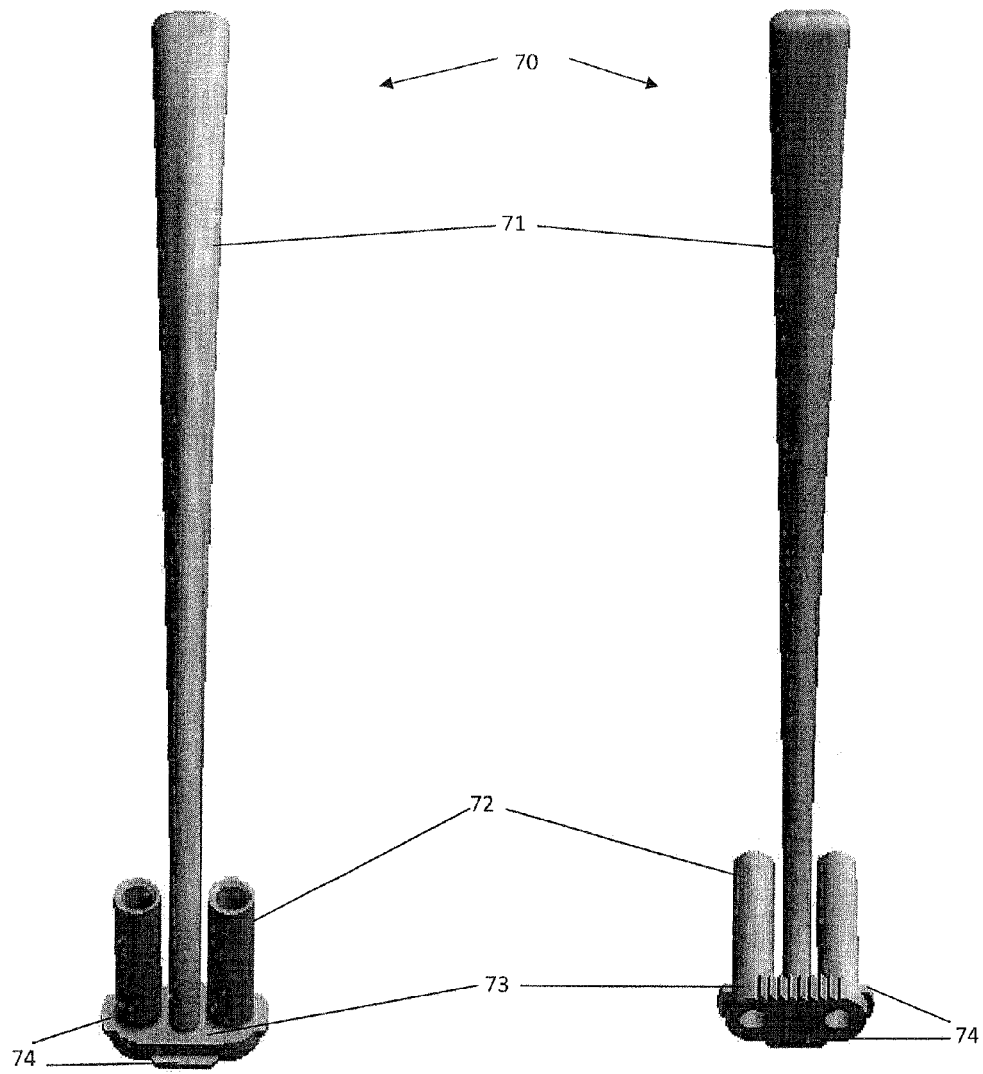
FIGS. 22 and 23 are front and rear perspectives, respectively, of a CAD rendering of the rack insert drill guide assembly 70.

Next the pinion driver tool 80 is placed over the pinion axle assembly 50 as shown in FIGS. 19-20. The pinion driver is rotated thereby rotating the pinion gear until the desired compression is achieved. At this time it is optional to open the fracture to facilitate the introduction of material such as bone paste or other materials that facilitate healing. If compression has been allowed to lapse, re-establish compression, lock the pinion gear and proceed to install bone screw 90 in position E (FIG. 21), This position is the last or end-most position of the compression plate and serves to establish the distance between the first screw in position A and the last position. At this time the next two screws can be installed at positions B and C. Now the pinion axle assembly can be removed and replaced with one or two bone screws with the assistance of the rack insert. Release compression and remove the pinion axle assembly (FIG. 21). Install the optional rack insert drill guide assembly 70 (FIGS. 22-23). Although optional, the use of the drill guides and bushings helps ensure that there is no off-axis loading or unwanted force bias put on the plate, Pinion Axle Assembly or bone screws.

Figure 24:
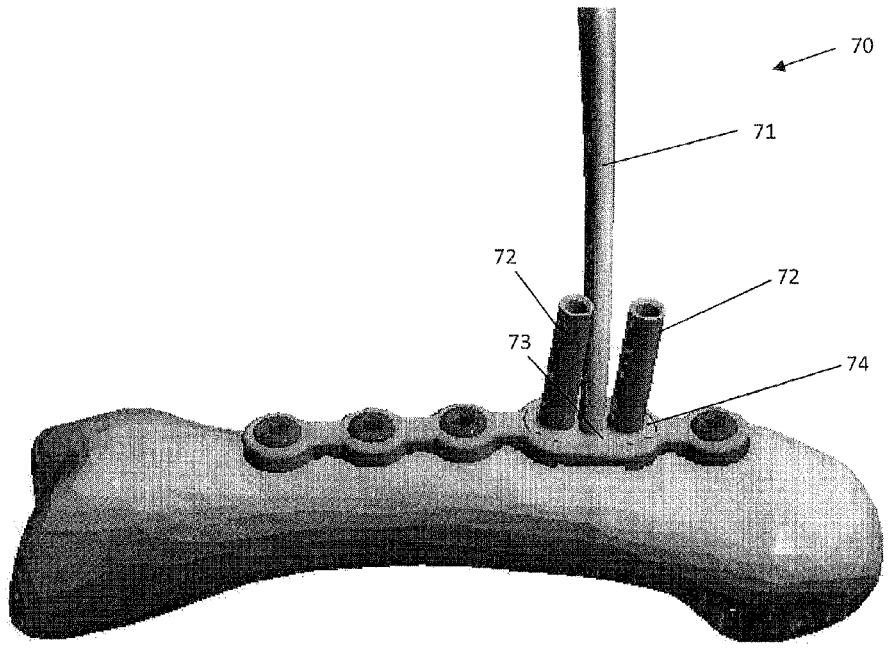
FIG. 24 is a frontal elevational perspective of a CAD rendering of the compression plate with the rack insert drill guide assembly 70 installed.
Figure 25:
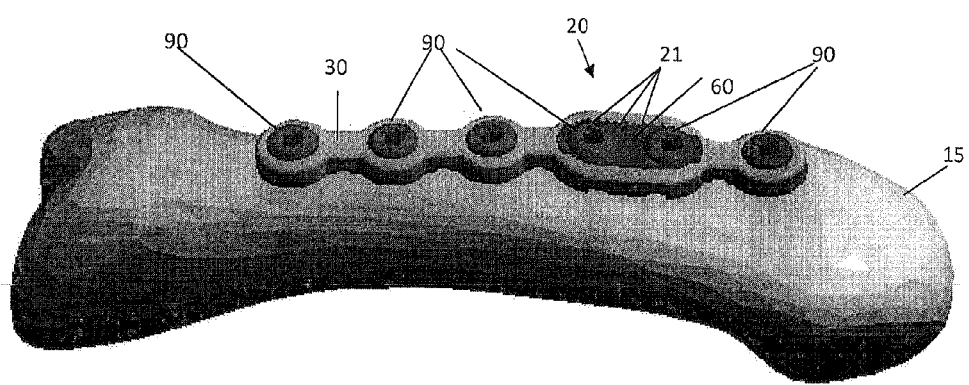
FIG. 25 is an elevational perspective of the compression plate with bone screws installed in positions A, B, C and E and a 2-screw insert installed in position D.
Figure 26:
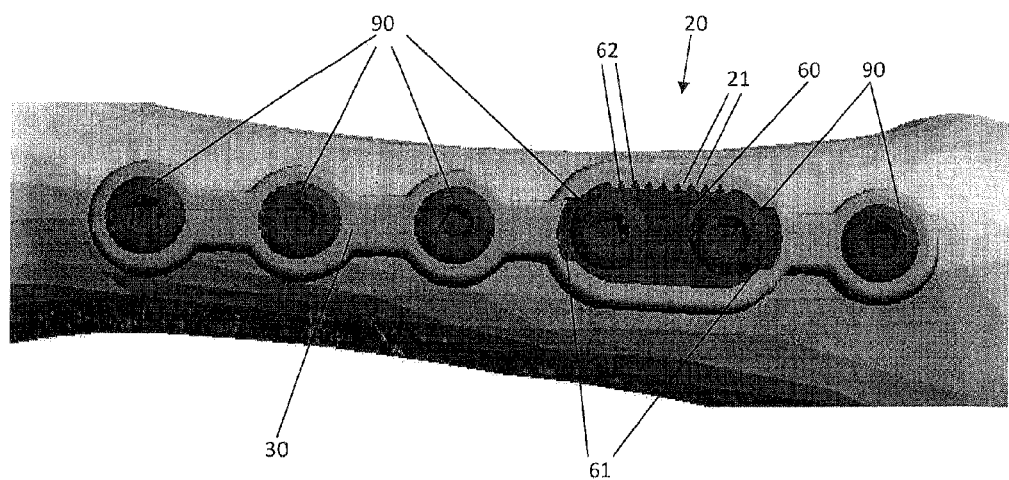
FIG. 26 is a close-up shot of FIG. 25.
Figures 30, 31:
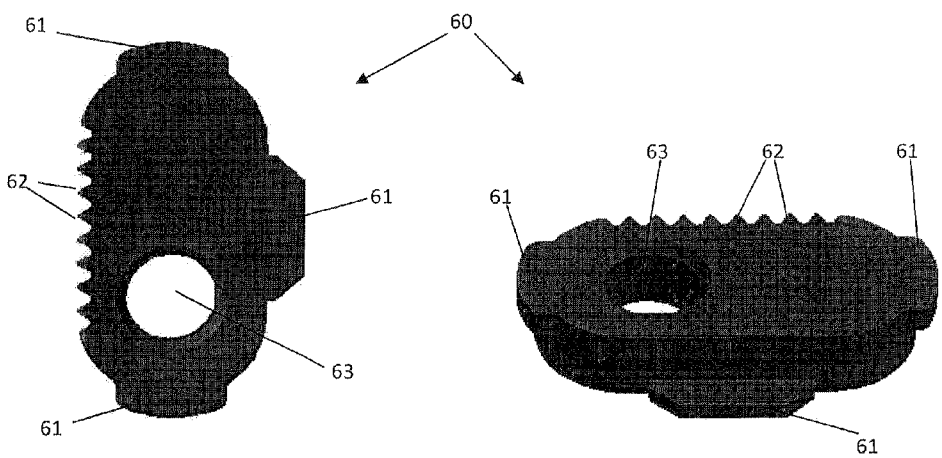
FIGS. 30-32 are different perspectives of the 1-screw rack insert.
Figures 32, 33:
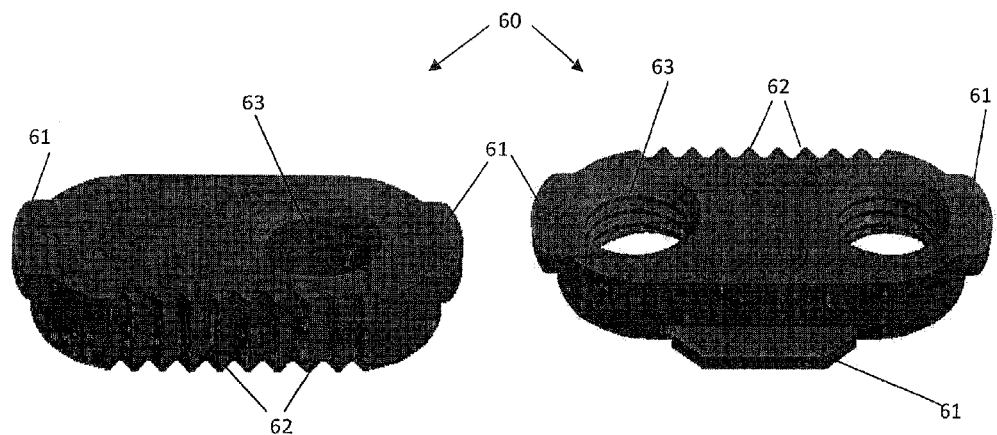
FIG. 33 is a front elevational perspective CAD rendering of a 2-screw rack insert.
Figure 34:
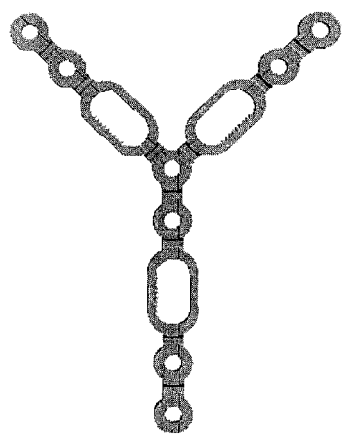
FIGS. 34-37 show composite embodiments of the compression plate in shapes resembling "Y," "T," "H" and a snowflake, respectively.
Figure 35:
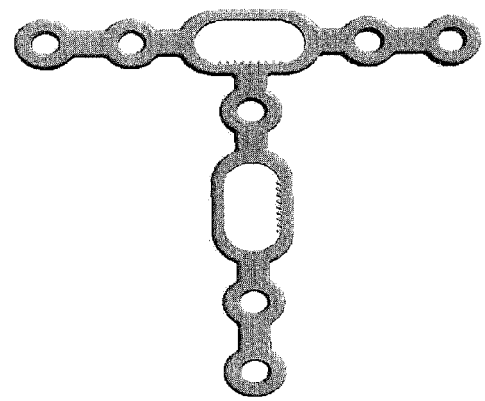
Figure 36:
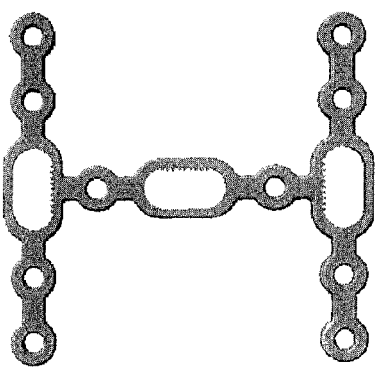
Figure 37:
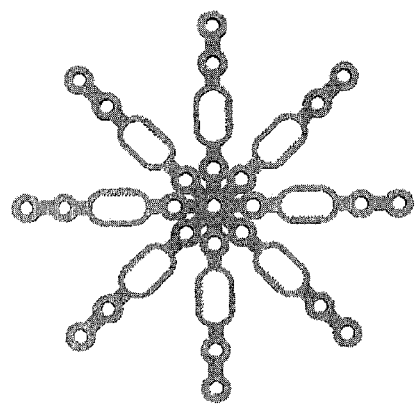

The rack insert drill guide assembly in the embodiment shown in FIGS. 22-23 comprises a handle 71 and the drill guide insert 73. Drill guide insert 73 further comprises two drill guides 72 and drill guide tabs 74 for positioning the drill guide in the insert positioning cutouts 22a,b and drill guide cutout 23 (FIG. 2). FIG. 24 shows the rack insert drill guide assembly installed in the elongate hole 36. The drill guides are now used to pre-drill two pilot holes for the rack insert shown in FIG. 33 which are then filled with two bone screws 90 at position D (FIGS. 25-26). The 1-screw insert of FIGS. 30-32 may also be used if desired. The compression plate is now installed. The surgical procedure is completed by closing the site.

The embodiments of the invention also comprise kits that include one or more of the compression plate apparatus of varying sizes and diameters to fit the application, bone screws, driver tools, drills and drill bits, rack inserts, drill guides, and a case for holding the tools and parts. Components of the kit may be sterile and/or sterilizable (e.g., autoclavable). In some examples, components of the kit, such as compression plate apparatus and/or bone screws, may be intended for single use. In some examples, components of the kit, such as drills, drill guides and/or drivers, may be intended or suitable for repeated use.

The following Table 2 is a listing of numbers for the various parts in the embodiments represented in the Figures. It is presented for purposes of clarity only and is not intended to be used to limit the embodiments of the invention in any way.

TABLE 2

| Number | Part name |
| --- | --- |
| 10 | Compression plate assembly |
| 12 | Latitudinal channel |
| 14 | Longitudinal channel |
| 15 | Bone |
| 17 | Fracture |
| 20 | Rack |
| 21 | Rack teeth |
| 22a, b | Insert positioning cutouts a (left), b (right) |
| 23 | Drill guide cutout |
| 30 | Plate |
| 32 | Bone screw holes |
| 34 | Bone screw hole threads |
| 36 | Elongate hole |
| 50 | Pinion axle assembly |
| 51 | Pinion drive pattern |
| 52 | Pinion gear |
| 53 | Pinion gear teeth |
| 54 | Pinion axle |
| 55 | Pinion head |
| 56 | Pinion threaded end |
| 57 | Pinion threads |
| 58 | Pinion head lip |
| 60 | Rack insert |
| 61 | Alignment tabs |
| 62 | Rack insert teeth |
| 63 | Rack insert bone screw hole |
| 65 | Bone screw drill guide |
| 66 | Bone screw drill guide threads |
| 67 | Bone screw drill guide neck |
| 68 | Bone screw drill guide collar |
| 70 | Rack insert drill guide assembly |
| 71 | Rack insert drill guide handle |
| 72 | Rack insert drill guide |
| 73 | Rack insert drill guide insert |
| 74 | Rack insert drill guide tabs |
| 75 | Pinion placement drill guide assembly |
| 76 | Pinion placement drill guide handle |
| 77 | Pinion placement drill guide insert |
| 78 | Pinion placement drill guide |
| 79 | Pinion placement drill guide insert tabs |
| 80 | Pinion driver tool |
| 81 | Pinion driver tool body |
| 82 | Pinion driver tool teeth |
| 83 | Pinion driver tool handle |
| 84 | Pinion driver tool shoulder |
| 85 | Pinion driver tool lumen |
| 90 | Bone screw |

It will be understood that various modifications may be made to the embodiments disclosed herein. Therefore, the above description should not be construed as limiting, but merely as exemplifications of preferred embodiments. Those skilled in the art will envision other modifications that come within the scope and spirit of the claims appended hereto. All patents and references cited herein are explicitly incorporated by reference in their entirety.

We claim:

1. A compression plate apparatus for stabilizing bone fragments with compression comprising:
 a. a plate having at least two bone screw holes adapted to accept at least one bone screw each, the plate additionally having at least one elongate hole through the plate;
 b. a rack comprising rack teeth located along at least one linear edge of the elongate hole;
 c. a pinion axle assembly comprising a pinion axle having a head portion, a pinion gear having complementary gear teeth for engaging the rack teeth and a lower portion having threads for engaging bone, whereby when a first bone screw is anchored in bone through a bone screw hole in the plate and the pinion axle assembly is anchored in a portion of bone across a fracture from the anchored bone screw through the elongate hole in the plate, then rotation of the pinion gear causes sliding motion of the unanchored bone fragment relative to the plate.

2. The apparatus of claim 1 wherein the bone screw hole further comprises threads adapted to engage with the first bone screw.

3. The apparatus of claim 1 wherein the first bone screw is adapted to lock into the bone screw hole.

4. The apparatus of claim 1 further comprising at least two bone screw holes in the plate on a first side of a fracture, and at least two bone screw holes on a second side of a fracture.

5. The apparatus of claim 1 wherein the pinion gear rides on the axle up to the head portion where it stops.

6. The apparatus of claim 5 wherein the pinion gear external diameter is smaller than the external diameter of the pinion head.

7. The apparatus of claim 1 wherein the rack teeth are machined from the plate.

8. The apparatus of claim 1 wherein the rack teeth are made from a separate material and are affixed to the plate.

9. The apparatus of claim 1 wherein the plate is rectangular in overall shape.

10. The apparatus of claim 1 wherein the plate is curvilinear in overall shape.

11. The apparatus of claim 1 wherein the plate has a plurality of elongate holes each having rack teeth therein.

12. A composite compression plate apparatus for stabilizing at least one bone fracture with compression comprising a plurality of compression plate apparatus of claim 1.

13. The apparatus of claim 12 wherein each individual compression plate is joined at one end to at least one other.

14. The apparatus of claim 12 wherein the plate is shaped in the form of an "H."

15. The apparatus of claim 12 wherein the plate is shaped in the form of a "Y."

16. The apparatus of claim 12 wherein the plate is shaped in the form of a "T."

17. The apparatus of claim 1 wherein the pinion gear locks to the plate.

18. The apparatus of claim 17 wherein the pinion gear locks to the rack.

19. The apparatus of claim 1 wherein the pinion gear locks to the pinion axle.

20. The apparatus of claim 1 wherein the pinion axle assembly further comprises a freewheeling clutch.

21. The apparatus of claim 20 wherein the freewheeling clutch comprises a sprag-type clutch.

22. A kit comprising the compression plate apparatus of claim 1, bone screws, a rack insert, drill bits, a pinion driver tool and a rack insert drill guide assembly.

23. A compression plate apparatus for stabilizing bone fragments with compression comprising:
   a. a plate having at least two bone screw holes adapted to accept at least one bone screw each, the plate additionally having at least one elongate hole through the plate;
   b. a rack comprising rack teeth located along at least one linear edge of the elongate hole;
   c. a pinion axle assembly comprising a pinion axle having a head portion, a pinion gear having complementary gear teeth for engaging the rack teeth, a lower portion having threads for engaging bone and a freewheeling clutch,
   whereby when a first bone screw is anchored in bone through a bone screw hole in the plate and the pinion axle assembly is anchored in a portion of bone across a fracture from the anchored bone screw through the elongate hole in the plate, then rotation of the pinion gear causes sliding motion of the unanchored bone fragment relative to the plate.

* * * * *

UNITED STATES PATENT AND TRADEMARK OFFICE
CERTIFICATE OF CORRECTION

PATENT NO. : 8,685,067 B2  
APPLICATION NO. : 13/326068  
DATED : April 1, 2014  
INVENTOR(S) : King et al.

It is certified that error appears in the above-identified patent and that said Letters Patent is hereby corrected as shown below:

References Cited, OTHER PUBLICATIONS, title page, col. 2, line 16, add missing publication:
--International Search Report and the Written Opinion, dated 04/10/12 (10 pgs)--.

Signed and Sealed this
Twenty-sixth Day of August, 2014

Michelle K. Lee
*Deputy Director of the United States Patent and Trademark Office*